United States Patent
Tanaka

(10) Patent No.: US 9,273,785 B2
(45) Date of Patent: Mar. 1, 2016

(54) FLOW CHANNEL SWITCHING VALVE

(71) Applicant: SHIMADZU CORPORATION, Kyoto-shi, Kyoto (JP)

(72) Inventor: Shinji Tanaka, Osaka (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 79 days.

(21) Appl. No.: 14/196,091

(22) Filed: Mar. 4, 2014

(65) Prior Publication Data

US 2014/0261815 A1 Sep. 18, 2014

(30) Foreign Application Priority Data

Mar. 15, 2013 (JP) .................. 2013-052928

(51) Int. Cl.
*F16K 11/074* (2006.01)
*F16K 31/04* (2006.01)
*G01N 30/20* (2006.01)

(52) U.S. Cl.
CPC ........... *F16K 11/0743* (2013.01); *F16K 31/041* (2013.01); *G01N 30/20* (2013.01); *G01N 2030/202* (2013.01); *Y10T 137/86622* (2015.04); *Y10T 137/86638* (2015.04)

(58) Field of Classification Search
CPC ................. G01N 2030/202; Y10T 137/86863; F16K 11/074; F16K 11/0743
See application file for complete search history.

(56) References Cited

U.S. PATENT DOCUMENTS

| | | | | |
|---|---|---|---|---|
| 3,297,053 | A * | 1/1967 | McKinney | 137/625.46 |
| 4,393,726 | A * | 7/1983 | Tamm et al. | 73/864.84 |
| 4,444,066 | A * | 4/1984 | Ogle et al. | 73/863.72 |
| 4,550,742 | A * | 11/1985 | Stearns | 137/14 |
| 4,655,095 | A * | 4/1987 | Russo et al. | 73/864.83 |
| 5,419,208 | A * | 5/1995 | Schick | 73/863.73 |
| 6,193,213 | B1 * | 2/2001 | Stearns et al. | 251/175 |
| 6,910,503 | B2 * | 6/2005 | Schick et al. | 137/625.47 |

FOREIGN PATENT DOCUMENTS

JP 2008-215494 A 9/2008

* cited by examiner

*Primary Examiner* — John Fox
(74) *Attorney, Agent, or Firm* — Westerman, Hattori, Daniels & Adrian, LLP

(57) ABSTRACT

A flow channel switching valve is provided including a stator and a rotor inside a housing, in which the rotor is rotated by a rotor drive portion while sliding on the stator. A rotor drive shaft holding the rotor is biased to a housing top side by an elastic member. A drive shaft stopper is provided that limits movement when the rotor drive shaft moves to the housing top side from a normal position when a housing top is attached to a housing body.

3 Claims, 4 Drawing Sheets

FLOW CHANNEL SWITCHING VALVE

BACKGROUND OF THE INVENTION

1. Field of the Invention

The present invention relates to a flow channel switching valve for use in, for example, an auto-sampler that introduces a sample to an analysis flow channel of a liquid chromatograph.

2. Description of the Related Art

As an example, in an auto-sampler that introduces a sample to an analysis flow channel of a liquid chromatograph, after the sample is taken into a sample loop from a sample container, the sample loop is connected to an upstream side of a separation column in the analysis flow channel by switching of a flow channel switching valve, which allows the sample in the sample loop to be transported to a separation column side by a mobile phase flowing in the analysis flow channel.

As the flow channel switching valve for use in the liquid chromatograph, a rotary type switching valve is common. The rotary type switching valve switches a connected flow channel by rotating a rotor (rotary part) (e.g., refer to Unexamined Japanese Patent Publication No. 2008-215494).

In the rotary type switching valve, a plurality of connection ports for connecting flow channel piping are provided in an upper portion of a housing, and a rotor and a stator (stationary part) are contained inside the housing. In the housing, the upper portion (hereinafter, a housing top) of the housing provided with the connection ports is detachable from a body of the housing (hereinafter, a housing body), and the exchange of parts such as the rotor, the stator, and the like is performed in a state where the housing top is detached from the housing body. The rotor and the stator are in contact with each other in a state where planes thereof keep liquid tightness with each other, and the stator is fixed by a pin or the like so as not to rotate with respect to a housing side. The connection ports communicate with the rotor through flow channels provided in the housing and holes of the stator. A groove forming a flow channel connecting between the connection ports is provided in a surface on a stator side of the rotor, and driving and rotating the rotor while sliding on the stator changes a position of the groove, thereby switching connection between the connection ports. There is also a rotary type switching valve in which a stator is integrated with the housing top.

The rotor is held by a forefront portion of a rotor drive shaft extending to a housing top side from a housing body side. A rotational mechanism that rotates the rotor drive shaft, such as a motor and the like, is provided on a base end side of the rotor drive shaft, and rotating the rotor drive shaft allows the rotor to be rotated. In order to keep the liquid tightness between the rotor and the stator, generally, a spring extendable in an axial direction of the rotor drive shaft is contained in a compressed state inside the housing body, and biases the rotor drive shaft to the housing top side by an elastic force of the spring, which increases a contact pressure between the rotor and the stator.

When inspection of an inside of the valve or exchange of consumable stores such as the rotor and the like are performed, the housing top needs to be detached from the housing body. The housing top is attached to the housing body by a plurality of bolts, and when the bolts are loosened, the spring pushing the rotor drive shaft to the housing top side tries to return to a natural length, thereby largely lifting the rotor drive shaft, and at this time, there may be posed problems that a contact pressure applied to the rotor is largely biased, thereby damaging the rotor, and the like. Thus, the respective bolts need to be loosened evenly little by little (e.g., by 90° or the like), and the detachment of the housing top needs to be performed carefully. Similarly, when the housing top is attached to the housing body, the bolts need to be fastened carefully to make the contact pressure on the rotor even.

SUMMARY OF THE INVENTION

An object of the present invention is to make easy detachment of a housing top from a housing body and attachment of the housing top to the housing body, and enhance maintainability of a flow channel switching valve.

A flow channel switching valve according to the present invention includes a stator and a rotor inside a housing, in which the rotor is rotated by a rotor drive portion while sliding on the stator. A rotor drive shaft holding the rotor is biased to a housing top side by an elastic member. A drive shaft stopper is provided that limits movement when the rotor drive shaft moves to the housing top side from a normal position when a housing top is attached to a housing body.

The housing is configured by the housing top and a housing body so as to have an internal space. The housing top has a plurality of connection ports connecting flow channel piping in an outer surface, and has, on a side of the internal space, a flow channel connection portion where connection holes respectively leading to the connection ports are arranged on one plane. The housing body has a depressed portion with a top open inside thereof, and detachably holds the housing top on an open portion of the depressed portion.

The stator is arranged inside the internal space of the housing, has through-holes corresponding to the connection holes of the flow channel connection portion, respectively, and is attached to the housing top side while keeping liquid tightness to the flow channel connection portion in a state where these through-holes are positioned at the connection holes. The stator may be detachably attached to the housing top, or may be configured integrally with the housing top.

The rotor is arranged inside the internal space of the housing, has a plane in contact with a surface of the stator on an opposing side of the flow channel connection portion, and is provided with a groove in the plane, the groove forming a flow channel selectively connecting between any one pair of the through-holes of the stator.

A rotor drive portion is provided on a housing body side, includes a rotor drive shaft extending from the housing body side to the housing top side to hold the rotor at a forefront portion on the housing top side, and rotates the rotor by rotating the rotor drive shaft with an axial center thereof as a rotation center.

The elastic member is contained in the housing body so as to be extendable in an axial direction of the rotor drive shaft, is in a compressed state when the rotor drive shaft is at a normal position, that is, a position when the housing top is attached to the housing body, and biases the rotor drive shaft at the normal position to the housing top side.

As a configuration that limits movement when the rotor drive shaft moves to the housing top side from the normal position, a first engagement portion provided in the rotor drive shaft and a second engagement portion provided in the housing body are arranged. The second engagement portion is arranged on the housing top side with respect to the first engagement portion, and both the engagement portions are apart from each other when the rotor drive shaft is at the normal position. When the rotor drive shaft moves to the housing top side from the normal position, the first engagement portion and the second engagement portion are engaged with each other, which inhibits the rotor drive shaft from moving to the housing top side any more.

The "rotor drive shaft" used herein includes a rotor holding portion at a forefront of the rotor drive shaft, and the first engagement portion making up the drive shaft stopper may be provided in a shaft portion of the rotor drive shaft, or may be provided in the rotor holding portion.

The flow channel switching valve of the present invention includes the drive shaft stopper that is made up of the first engagement portion provided on a rotor drive shaft side and the second engagement portion provided on the housing body side, and limits the movement to a forefront side of the rotor drive shaft by engaging the first engagement portion and the second engagement with each other when the rotor drive shaft moves from the normal position to a position on the forefront side of the rotor drive shaft, and on a base end side of the rotor drive shaft with respect to a position where the elastic member reaches a natural length, and thus, the rotor drive shaft is stopped at the position before the elastic member returns to the natural length when the housing top is detached from the housing body, and an amount of rise of the rotor drive shaft is small. This reduces a loosening amount of bolts needed when the housing top is detached from the housing body, and a fastening amount of the bolts needed when the housing top is attached to the housing body, which makes it easy to evenly loosen or fasten the respective bolts. This makes attachment/detachment of the housing top with respect to the housing body easy, and enhances the maintainability.

DETAILED DESCRIPTION OF THE INVENTION

As a drive shaft stopper in a flow channel switching valve of the present invention, a first engagement portion may be provided as a projected portion that is projected to a housing body side from an outer circumferential surface of a rotor drive shaft, and a second engagement portion may be provided as a projected portion that is projected to a rotor drive shaft side from an inner circumferential surface of a housing body.

According to a preferred aspect of the above-described case, the first engagement portion is a flange-shaped projected portion provided along the outer circumferential surface of the rotor drive shaft, and the second engagement portion is a ring-shaped projected portion provided along the inner circumferential surface of the housing body. According to the above-described aspect, the rotor drive shaft is evenly held and stopped in a circumferential direction, and thus, a posture of the rotor drive shaft is prevented from being slanted, and a biased contact pressure is prevented from being applied to a rotor.

Figure 1:
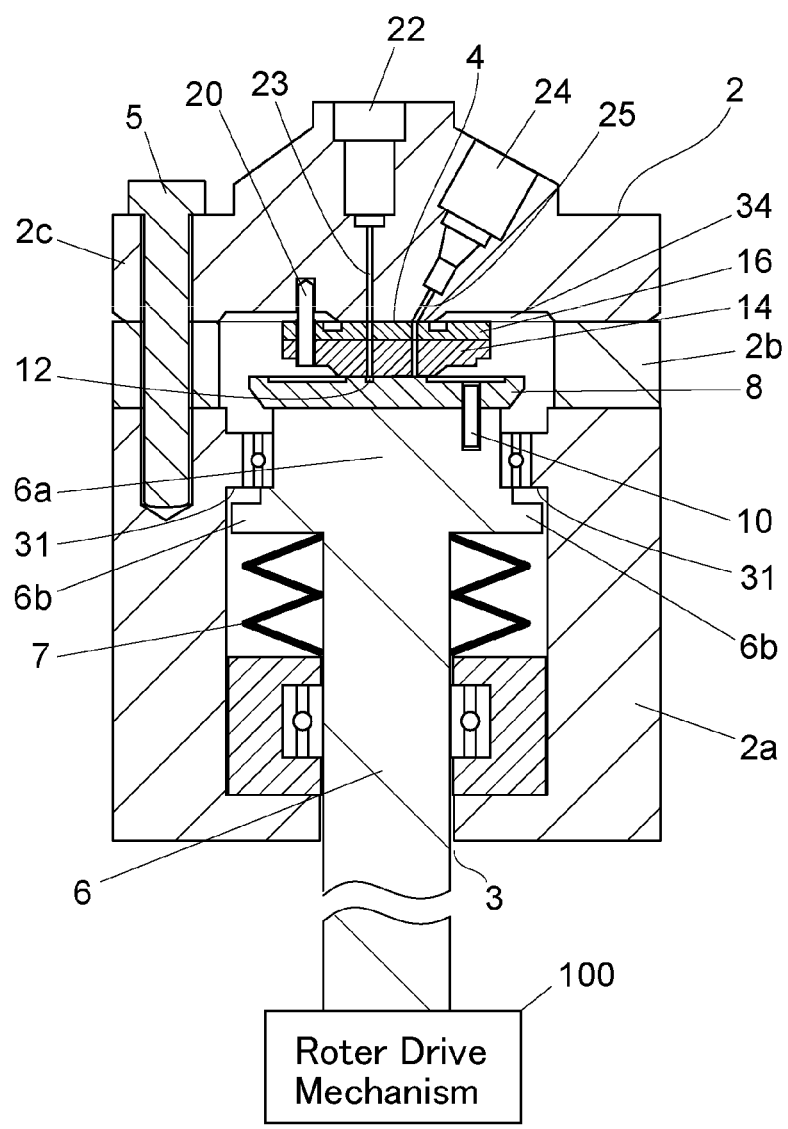
FIG. 1 is a cross-sectional view showing one embodiment of a flow channel switching valve.

One embodiment of a flow channel switching valve will be described with reference to FIG. 1.

In an internal space of a housing 2, a rotor 8 as a rotary part, and a stator 14 as a stationary part are contained. The housing 2 is circular in a planar shape, and includes a plurality of connection ports 22, 24 connecting flow channel piping in an upper outer surface. In a central portion of a lower surface of the housing 2, a hole 3 is provided, and a rotor drive shaft 6 that rotates the rotor 8 penetrates the hole 3. The rotor drive shaft 6 is supported rotatably by a bearing inside the housing 2, and is coupled to a rotor drive mechanism 100 that rotates the rotor drive shaft 6 outside the housing 2. The rotor drive shaft 6 and the rotor drive mechanism 100 make up a rotor drive portion.

The housing 2 is made up of three members of a housing body 2a, an intermediate member 2b, and a housing top 2c. The housing body 2a has a cylindrical shape, and the hole 3 is opened at a center of a seating surface. In a state where an opening of the housing body 2a is in an upward direction, the ring-shaped intermediate member 2b is placed on the opening, and the disc-shaped housing top 2c is placed on the intermediate member 2b. The housing body 2a serves as a base for the housing 2, and the intermediate member 2b and the housing top 2c are detachably attached to the housing body 2a by bolts 5. The bolts 5 are fastened so as to penetrate the intermediate member 2b from an upper surface side of the housing top 2c located in an upmost portion of the housing 2 and reach the housing body 2a. The housing top 2c is provided with through-holes through which the bolts 5 penetrate the housing top 2c, and the intermediate member 2b is also provided with through-holes 54 through which the bolts 5 penetrate the intermediate member 2b (refer to FIG. 2). The housing body 2a is provided with screw holes 56 to fasten the bolts 5 (refer to FIG. 2). Although in FIG. 1, only one attachment position of the bolts 5 is illustrated, the bolts 5 are attached at three even positions in a circumferential edge portion on a plane viewed from an upper surface side of an upper surface of the housing top 2c. The attachment positions of the bolts 5 are not limited thereto.

In a lower surface of the housing top 2c, which is an inner wall surface of the housing 2, a flow channel connection portion 4 is provided. The flow channel connection portion 4 is a plane where holes of end portions of flow channels 23, 25 leading to the connection ports 22, 24 are arrayed, and the stator 14 is in contact with the flow channel connection portion 4 with a packing 16 interposed. The flow channel connection portion 4 is a circular plane region with an outer circumference surrounded by a ring-shaped depression 34. The stator 14 and the packing 16 are each a circular member larger than the flow channel connection portion 4 in a planar shape, and a central portion of the packing 16 is in contact with the flow channel connection portion 4 while keeping liquid tightness. The stator 14 may be integrated with the housing top 2c, or may be configured as a separate body.

The rotor 8 is rotated by the rotor drive shaft 6 inside the housing 2. The rotor drive shaft 6 is arranged perpendicular to the plane of the flow channel connection portion 4, and is provided with a rotor holding portion 6a at a forefront. A forefront surface of the rotor holding portion 6a is a plane parallel to the flow channel connection portion 4, and the rotor 8 is in contact with the stator 14 by being held by the forefront surface of the rotor holding portion 6a. A base end portion of the rotor drive shaft 6 is led outside the housing 2 through the hole 3 of the housing 2 to be rotated around a shaft center thereof by the rotor drive mechanism 100 including a rotation mechanism such as a motor and the like outside the housing 2. In order to hold the rotor 8 in the rotor holding portion 6a by a rotor fixing pin 10, the rotor 8 is provided with a though-hole 58 (refer to FIG. 2) to cause the rotor fixing pin 10 to penetrate the rotor 8, and the rotor holding portion 6a is provided with a hole 60 (refer to FIG. 2) into which the rotor fixing pin 10 is inserted. In this manner, the rotor 8 is inhibited from rotating with respect to the rotor holding portion 6a, and the rotor 8 is rotated by the rotation of the rotor drive shaft 6.

A spring 7, such as a disc spring, a coil spring, and the like, in a compressed state is inserted between a bottom portion of the housing body 2a and the rotor holding portion 6a, and the rotor drive shaft 6 is biased to a housing top 2c side by the spring 7. This allows the rotor 8 to be pressed to the stator 14. In a surface on the stator 14 side of the rotor 8, a groove 12 is provided that forms a flow channel connecting flow channels of any one pair of the plurality of flow channels 23, 25 of the housing top 2c, and a position of the groove 12 is changed by the rotation of the rotor 8.

When the rotor drive shaft 6 is rotated by the rotor drive mechanism 100, the position of the groove 12 is changed to switch the connection between the plurality of flow channels 23, 25 of the flow channel housing top 2c.

Figure 2:
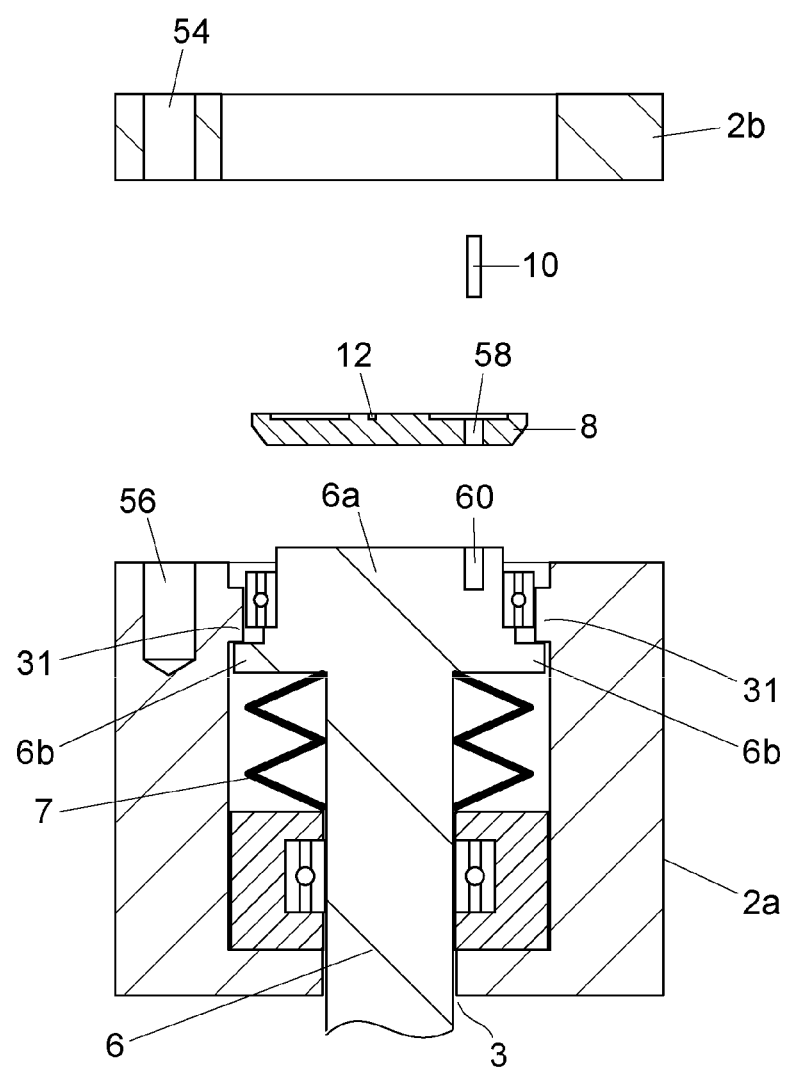
FIG. 2 is an exploded cross-sectional view of a housing body side of the same embodiment.

A structure of the housing body 2a side will be further described with reference to FIG. 2 as well as FIG. 1.

The rotor holding portion 6a has a columnar shape, and includes a projected portion 6b projected in a flange shape along the outer circumferential surface of a lower portion of the column. The housing body 2a is provided with a projected portion 31 having a rectangular cross section that is projected in a ring shape along the inner circumferential surface on the housing top 2c side. An inner diameter of the portion where the projected portion 31 is provided is smaller than an outer shape of the projected portion 6b, and slightly larger than an outer diameter of the rotor holding portion 6a above the projected portion 6b, and the projected portion 31 surrounds an outer circumference of the rotor holding portion 6a above the projected portion 6b with a slight clearance. The rotor holding portion 6a holds the rotor 8 above the projected portion 31. The projected portion 31 is not necessarily required to have the ring shape, but may be plurality of projections arranged along the inner circumferential surface on the housing top 2c side of the housing body 2a so as to be able to be engaged with the projected portion 6b of the rotor holding portion 6a.

Thereby, although the rotor drive shaft 6 tries to rise by an elastic force of the spring 7 when the housing top 2c is detached from the housing body 2a, the projected portion 6b of the rotor holding portion 6a is engaged with a lower surface of the projected portion 31 of the housing body 2a, so that the rotor drive shaft 6 stops at a position where the rotor drive shaft 6 rises up to a predetermined height. The projected portion 6b (the first engagement portion) and the projected portion 31 (the second engagement portion) make up the drive shaft stopper that limits the rising of the rotor drive shaft 6 by the spring 7 to the predetermined height.

The projected portion 6b and the projected portion 31 are provided with a positional relation in which they do not interfere with each other in a state where the housing top 2c is mounted on the housing body 2a, and it is not until the housing top 2c is detached from the housing body 2a and the rotor drive shaft 6 rises to the predetermined height that they interfere with each other. The predetermined height is a height before the spring 7 completely returns to the natural length.

While in this embodiment, the projected portion 6b is provided as the ring-shaped projection surrounding the outer circumferential surface of the rotor holding portion 6a, in the case where the projected portion 31 is ring-shaped, the projected portion 6b may have any shape such as a plurality of projections, as long as the projected portion 6b has a structure engaged with the projected portion 31 when the rotor drive shaft 6 rises up to the predetermined height.

The structure in which provision of the projected portion 6b and the projected portion 31 stops the rising of the rotor drive shaft 6 at the predetermined height can be applied to not only the flow channel switching valve in which the stator 14 is configured integrally with the housing top 2c but also a flow channel switching valve having a different structure from that of the flow channel switching valve of this embodiment.

Figure 3:
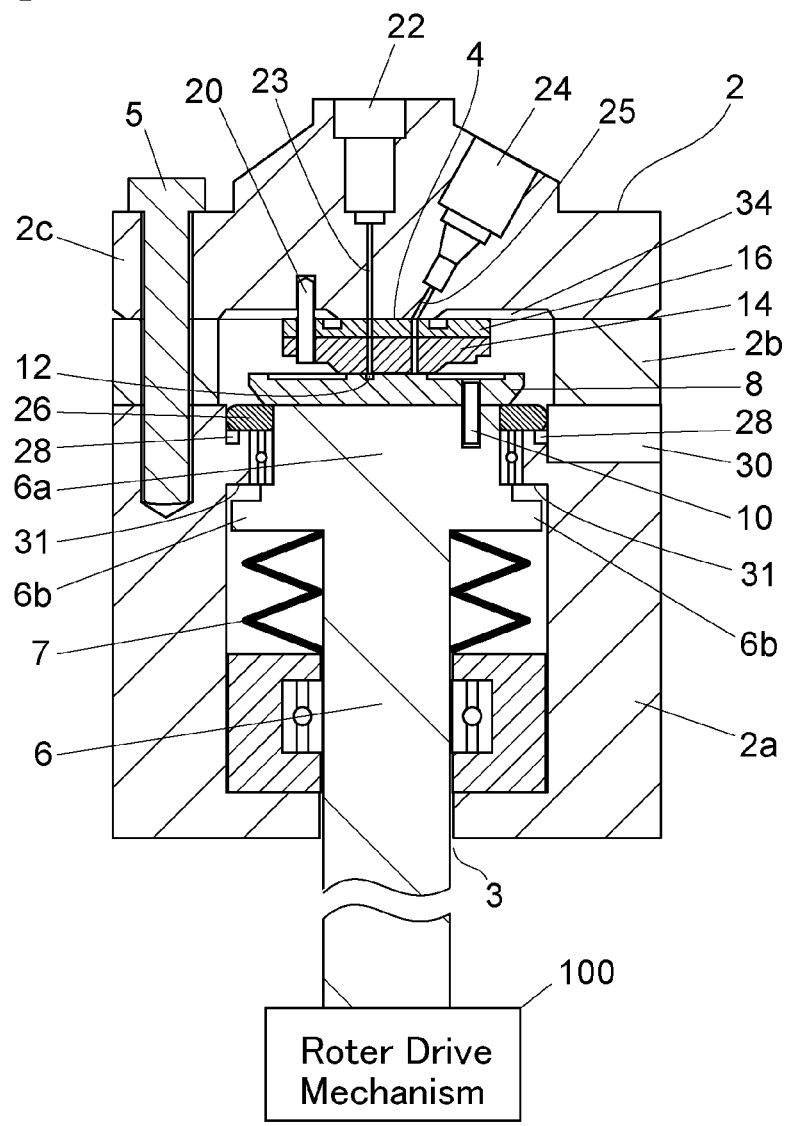
FIG. 3 is a cross-sectional view showing another embodiment of the flow channel switching valve.
Figure 4:
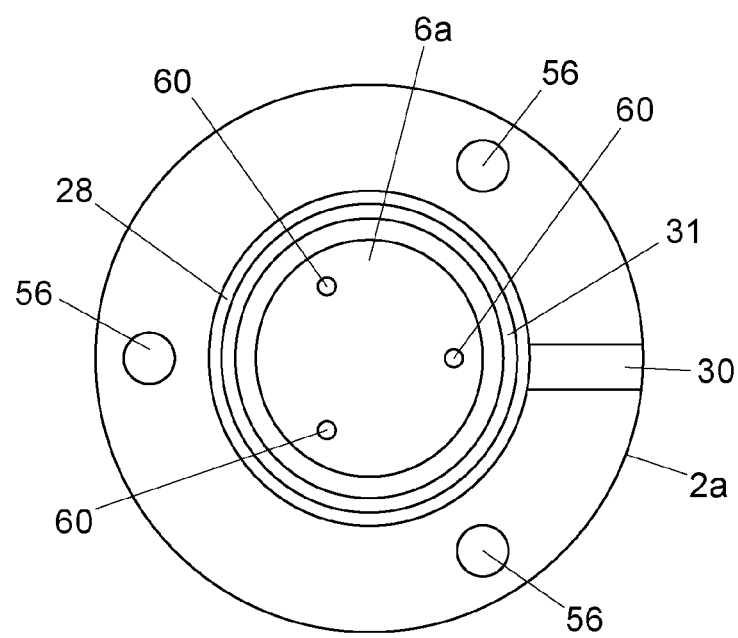
FIG. 4 is a plane view of the housing body side of the same embodiment as seen from above in a state where a rotor and a seal ring are detached.

Hereinafter, an embodiment in which the present invention is applied to the flow channel switching valve having a different structure from that of the above-described embodiment will be described with reference to FIGS. 3 and 4. In the following, the same reference numerals are given to the same portions as those in the above-described embodiment, and descriptions thereof are omitted.

In this embodiment, a ring-shaped seal ring 26 is arranged between the inner circumferential surface of the housing body 2a and the outer circumferential surface of the rotor holding portion 6a at a position above the projected portion 31. The seal ring 26 tightly adheres to the outer circumferential surface of the rotor holding portion 6a above the projected portion 6b to seal the clearance between the rotor holding portion 6a and the projected portion 31. As a material of the seal ring 26, a resin such as PDMS (polydimethylsiloxane) and PTFE (polytetrafluoroethylene) is preferable.

In an upper surface of the projected portion 31, a ring-shaped groove 28 with a top open is provided along the inner circumferential surface of the housing body 2a at a border portion with the inner circumferential surface of the housing body 2a. At one position of an end surface on the housing top 2c side of the housing body 2a, a groove 30 is provided leading the groove 28 outside the housing 2. The groove 28 guides liquid leaking from between the rotor 8 and the stator 14 to the groove 30, and the groove 30 discharges the liquid guided by the groove 28 outside the housing 2.

Since the seal ring 26 is in contact with the upper surface of the projected portion 31, the liquid leaking from between the rotor 8 and the stator 14 moves along an upper surface of the seal ring 26. Since the seal ring 26 tightly adheres to the outer circumferential surface of the rotor holding portion 6a, the liquid does not enter between the seal ring 26 and the rotor holding portion 6a, and the leaking liquid moves in an outside direction along the upper surface of the seal ring 26. At the position just below a circumferential edge portion of the seal ring 26, the groove 28 is provided, and the liquid that reaches the circumferential edge portion of the seal ring 26 is guided to the groove 30 by the groove 28, thereby being discharged outside the housing 2.

In order to make it easy to guide the liquid leaking out onto the upper surface of the seal ring 26 to the groove 28, an outer side of the upper surface of the seal ring 26 is inclined so as to moderately decline toward the circumferential edge portion. While in FIG. 3, the outer side of the seal ring 26 has a rounded shape, a shape of the seal ring 26 may be any shape that can bring about an effect of making it easy to guide the liquid to the groove 28, such as a tapered shape on the outer side of the upper surface of the seal ring 26.

The structure in which the liquid leaking from between the rotor 8 and the stator 14 is discharged outside by the groove 28 and the groove 30 can also be applied to the flow channel switching valve having the different structure from the flow channel switching valve of this embodiment such as the flow channel switching valve in which the stator 14 is configured integrally with the housing top 2c, and the like.

What is claimed is:

1. A flow channel switching valve comprising:
   a housing that has an internal space, the housing including
   a housing top having a plurality of connection ports connecting flow channel piping in an outer surface thereof, and having, on a side of the internal space, a flow channel connection portion where connection holes respectively leading to the connection ports are arranged on one plane, and a housing body that has a depressed portion with a top open inside thereof and detachably holds the housing top on an open portion of the depressed portion;

a stator that is arranged inside the internal space of the housing, has through-holes corresponding to the connection holes of the flow channel connection portion, respectively, and is attached to a side of the housing top while keeping liquid tightness to the flow channel connection portion in a state where the through-holes are positioned at the connection holes;

a rotor that is arranged inside the internal space of the housing, has a plane in contact with a surface of the stator on an opposing side of the flow channel connection portion, and is provided with a groove in the plane, the groove forming a flow channel selectively connecting between any one pair of the through-holes of the stator;

a rotor drive portion that is provided on a side of the housing body, includes a rotor drive shaft extending from the side of the housing body toward the side of the housing top to hold the rotor at a forefront portion of the rotor drive shaft, on the side of the housing top, and rotates the rotor by rotating the rotor drive shaft with an axial center thereof as a rotation center;

an elastic member that is contained in the housing body so as to be extendable in an axial direction of the rotor drive shaft, is in a compressed state when the rotor drive shaft is at a normal position, which is a position when the housing top is attached to the housing body, and biases the rotor drive shaft at the normal position to the side of the housing top; and a drive shaft stopper that is made up of a first engagement portion provided in the rotor drive shaft, and a second engagement portion provided in the housing body, and limits movement of the rotor drive shaft to the side of the housing top by engaging the first engagement portion and the second engagement portion to each other when the rotor drive shaft moves to the side of the housing top from the normal position.

2. The flow channel switching valve according to claim 1, wherein the first engagement portion is a projected portion that is projected from an outer circumferential surface of the rotor drive shaft to the side of the housing body, and the second engagement portion is a projected portion that is projected from an inner circumferential surface of the housing body to a side of the rotor drive shaft.

3. The flow channel switching valve according to claim 2, wherein the first engagement portion is a flange-shaped projected portion provided along the outer circumferential surface of the rotor drive shaft, and the second engagement portion is a ring-shaped projected portion provided along the inner circumferential surface of the housing body.

* * * * *